(12) United States Patent
Diaz Peralta et al.

(10) Patent No.: US 10,524,469 B2
(45) Date of Patent: Jan. 7, 2020

(54) **ACETATE DERIVED COMPOUNDS FROM GERANYLORCINOL. SYNTHESIS PROCESS FOR OBTAINING SAID COMPOUNDS AND USE OF SAID COMPOUNDS AS ANTIFUNGAL AGAINST *BOTRYTIS CINEREA***

(71) Applicant: UNIVERSIDAD TÉCNICA FEDERICO SANTA MARÍA, Valparaíso (CL)

(72) Inventors: Katy Paulina Diaz Peralta, Valparaíso (CL); Luis Javier Espinoza Catalan, Valparaíso (CL); Floreal Andres Olea Carrasco, Valparaíso (CL); Hugo Alberto Peña Cortes, Valparaíso (CL); Lautaro Liber Taborga Morales, Valparaíso (CL)

(73) Assignee: UNIVERSIDAD TÉCNICA FEDERICO SANTA MARÍA, Valparaíso (CL)

( * ) Notice: Subject to any disclaimer, the term of this patent is extended or adjusted under 35 U.S.C. 154(b) by 0 days.

(21) Appl. No.: 15/546,910

(22) PCT Filed: Jan. 25, 2016

(86) PCT No.: PCT/CL2016/050004
§ 371 (c)(1),
(2) Date: Jul. 27, 2017

(87) PCT Pub. No.: WO2016/119074
PCT Pub. Date: Aug. 4, 2016

(65) Prior Publication Data
US 2018/0035669 A1    Feb. 8, 2018

(30) Foreign Application Priority Data

Jan. 27, 2015    (CL) .................................... 200-2015

(51) Int. Cl.
*A01N 31/16*    (2006.01)
*C07C 37/00*    (2006.01)
*C07C 39/19*    (2006.01)

(52) U.S. Cl.
CPC .............. *A01N 31/16* (2013.01); *C07C 37/00* (2013.01); *C07C 39/19* (2013.01)

(58) Field of Classification Search
CPC ........ A01N 31/16; A01N 27/00; C07C 15/02; C07C 37/00; C07C 39/19
See application file for complete search history.

(56) References Cited

FOREIGN PATENT DOCUMENTS

WO    WO2003082303    * 10/2003    ............. A61K 31/74

OTHER PUBLICATIONS

Croy et al. (Journal of Controlled Release 95 (2004) 161-171).*
Petu et al. (Polymers 2010, 2, 229-251).*
International Search Report and Written Opinion, International Patent Application No. PCT/CL2016/050004, dated Apr. 29, 2016, with English translation (21 pages).
Taborga et al., "Synthesis and NMR Structure Determination of New Linear Geranylphenols by Direct Geranylation of Activated Phenols", J. Chil. Chem. Soc., 58, N° 2, 2013.
Espinoza et al., "Synthesis of Linear Geranylphenols and Their Effect on Mycelial Growth of Plant Pathogen Botrytis cinerea", Molecules 19, pp. 1512-1526, Jan. 27, 2014.
Eisohly et al., "Synthesis and Antimicrobial Activities of Certain Cannabichromene and Cannabigerol Related Compounds", Journal of Pharmaceutical Sciences, vol. 71, No. 12, p. 1319-1323, Dec. 1982.
Luo et al., "Activity in vitro and in vivo against Plant Pathogenic Fungi of Grifolin Isolated from the Basidiomycete Albatrellus dispansus", Z. Naturforsch C. vol. 60, No. 1, pp. 50-61, Jan.-Feb. 2005.
Tsao et al., "Antifungal Activity of Monoterpenoids against Post-harvest Pathogens Botrytis cinerea and Monilinia fructicola", J. Essent. oil. Res., 12, pp. 113-121, Jan.-Feb. 2000.
Baeza et al., "Synthesis and Cytotoxic Activity of Geranylmethoxyhydroquinone Derivatives", J. Chil. Chem. Soc., 57, N° 3, 2012.
Manners et al., "Biogenetic-Type Syntheses of Isoprenoid and Diisoprenoid Derivatives of Orcinal", Tetrahedron, vol. 28, No. 11, pp. 2949-2959, 1972.

* cited by examiner

*Primary Examiner* — Robert H Havlin
(74) *Attorney, Agent, or Firm* — Hamre, Schumann, Mueller & Larson, P.C.

(57) ABSTRACT

The present invention discloses a synthesis process for obtaining linear derivative compounds from geranylorcinoles, said linear derivative compounds from geraniylorcinol, the acetylated derivatives compounds therefrom, the method for encapsulating the compounds in a polymer matrix and the use of said encapsulated compounds as antifungal against *Botrytis cinerea*.

7 Claims, No Drawings

ACETATE DERIVED COMPOUNDS FROM GERANYLORCINOL. SYNTHESIS PROCESS FOR OBTAINING SAID COMPOUNDS AND USE OF SAID COMPOUNDS AS ANTIFUNGAL AGAINST *BOTRYTIS CINEREA*

FIELD OF THE INVENTION

The present invention seeks protection on linear derivative compounds from geranylorcinol, on the acetylated derivative compounds thereof, on the synthesis process for obtaining said compounds and on the use of said compounds as antifungals against *Botrytis cinerea*.

BACKGROUND OF THE INVENTION

Linear geranylphenols are an interesting subclass of secondary metabolites found primarily in marine organisms. They are biosynthesized in a mixed form from the metabolic pathway of shikimic acid and mevalonic acid. The terpene portion may have a length of up to nine isoprene units, which chain originates from the mevalonate biosynthetic pathway while the aromatic portion is derived from the biosynthetic pathway of the shikimic acid. Among marine organisms in which this type of compound has been isolated are brown seaweed (Faulkner, D. *J. Natural Product Reports* 1986, 3, 1-33; Ochi, M.; Kotsuki, H.; Inoue, S.; Taniguchi, M. *Chemistry* 1979, 831-832; Capon, R. J.; Ghisalberti, E. L.; Jefferies, P. R. *Phytochemistry* 1981, 20, 2598-2600; Gerwick, W. H.; Fenical, W. The *Journal of Organic Chemistry* 1981, 46, 22-27), sponges (Rosa, S. De; Crispino, A., Giulio, A. De *Journal of Natural* 1995, 58, 1450-1454; Bifulco, G.; Bruno, I.; Minale, L.; Riccio, R.; Debitus, C.; Bourdy, G.; Vassas, A.; Lavayre, J. *Journal of Natural Products* 1995, 58, 1444-1449), alcyonaceas (Bowden, B. F.; Coll, J. C. *Australian Journal of Chemistry* 1981, 34, 2677-2681), gorgonaceas (Ravi, B. N.; Wells, R. J. *Australian Journal of Chemistry* 1982, 35, 105-112), ascidias (Howard, B. M.; Clarkson, K.; Bernstein, R. L. *Tetrahedron Letters* 1979, 20, 4449-4452; Targett, N. *Journal of Natural Products* 1984, 1696, 1975-1976; Guella, G.; Mancini, I.; Pietra, F. *Helvetica Chimica Acta* 1987, 70, 621-626; Faulkner, D. J. *Natural product reports* 1993, 10, 497-539; Fu, X.; Hossain, M. B.; Helm, D. Van Der; Schmitz, F. J.; Van der Helm, D. *Journal of the American Chemical Society* 1994, 116, 12125-12126; Fu, X.; Hossain, M. B.; Schmitz, F. J.; Helm, D. Van Der *The Journal of Organic Chemistry* 1997, 62, 3810-3819). From the brown algae, compounds with chains of the mono-, sesqui- and di-terpene type have been isolated whereas structures with long linear chains have been obtained from sponges.

For this family of compounds, potent biological activities have been reported including anti-inflammatory (Quang, D. N.; Hashimoto, T.; Arakawa, Y.; Kohchi, C.; Nishizawa, T.; Soma, G.-I.; Asakawa, Y. *Bioorganic & medicinal chemistry* 2006, 14, 164-8; Bauer, J.; Koeberle, A.; Dehm, F.; Pollastro, F.; Appendino, G.; Northoff, H.; Rossi, A.; Sautebin, L.; Werz, O. *Biochemical pharmacology* 2011, 81, 259-68), antifungal (Danelutte, A. P.; Lago, J. H. G.; Young, M. C. M.; Kato, M. J. *Phytochemistry* 2003, 64, 555-559), anti-HIV (Manfredi, K. P.; Vallurupalli, V.; Demidova, M.; Kindscher, K.; Pannell, L. K. *Phytochemistry* 2001, 58, 153-7), antioxidant (Yamaguchi, L. F.; Lago, J. H. G.; Tanizaki, T. M.; Mascio, P. Di; Kato, M. J. *Phytochemistry* 2006, 67, 1838-43), the most frequent of reported activities being the antineoplastic activity (Han, Q.-B.; Qiao, C.-F.; Song, J.-Z.; Yang, N.-Y.; Cao, X.-W.; Peng, Y.; Yang, D.-J.; Chen, S.-L.; Xu, H.-X. *Chemistry & biodiversity* 2007, 4, 940-6; Liu, Q.; Shu, X.; Wang, L.; Sun, A.; Liu, J.; Cao, X. *Cellular & molecular immunology* 2008, 5, 271-8).

Synthesis of Linear Geranylphenols

As we have seen, these compounds, whose structure combines a linear terpene unit with a phenolic portion and which have been isolated from various organisms, have been shown to possess a large number of biological properties. However, the major problem for the study of this group relates to its low yield for obtaining them from natural sources. Clearly this important structural group requires an overall strategy for the preparation of the natural products containing this pharmacophore as well as systems with other aromatic residues (Osorio, M.; Aravena, J.; Vergara, A.; Taborga, L.; Baeza, E.; Catalán, K.; González, C.; Carvajal, M.; Carrasco, H.; Espinoza, L. *Molecules* (Basel, Switzerland) 2012, 17, 556-70).

The most recurrent of the synthetic strategies used for the preparation of terpenylphenols consists, as a first step, of the separate preparation of the appropriate terpene and aromatic fragments for the synthesis. The second step is crucial to the success of the synthesis and involves coupling of the synthetic terpenyl equivalent to the aromatic nucleus. The most commonly used methods for anchoring the two portions are numbered in the following list:

1. Condensation of the terpene and the phenol (Friedel-Crafts allylation) catalysed by a Brönsted acid.
2. Direct terpenylation with terpenyltrialkyltin in the presence of a Lewis acid
3. Rearrangement of terpenylylether catalysed by a Lewis acid.
4. Nucleophilic substitution of aryllithium derivatives on alkyl halides.
5. Nucleophilic substitution of alkyllithium derivatives on aryl halides.
6. Nucleophilic addition of aryllithium derivatives to carbonyls of the terpenyl unit and subsequent reduction in the presence of a Lewis acid.
7. Condensation of geraniol and hydroquinone (Friedel-Crafts allylation) catalysed by a Lewis acid.

Condensation of Geraniol with Hydroquinone and Phenols (Friedel-Crafts Allylation) Catalysed by a Lewis Acid.

The most common direct geranylation schemes involves "π-excedent" aromatic compounds in a Friedel-Crafts alloy under acidic conditions (Keinan, E.; Eren, D. *The Journal of Organic Chemistry* 1987, 18, 3872-3875; Syper, L.; Kloc, K.; Mz.xl; lochowski, J. *Tetrahedron* 1980, 36, 123-129; Eisohly, H. N.; Turner, C. E.; Clark, A. M.; Eisohly, M. A. *Journal of Pharmaceutical Sciences* 1982, 71, 1319-23). Despite the number of modifications, these approaches are limited by the inherent instability of the allylic alcohol in the acidic conditions employed and undesirable side reactions (Stevens, K L, Jurd, L. Manners, G. *Tetrahedron* 1972, 28, 1939-1944). However, when acid catalysis, such as the reaction with oxalic acid, is replaced by the Lewis acid $BF_3 \cdot Et_2O$, reaction yields are considerably increased, in addition to using non-aqueous solvents such as ether, dioxane, $CH_2Cl_2$ and $CCl_4$. For this synthesis strategy, yields close to 60% are obtained (Fedorov, S.; Radchenko, O.; Shubina, L. *Pharmaceutical* 2006, 23, 70-81; Shubina, L. K.; Fedorov, S. N.; Radchenko, O. S.; Balaneva, N. N.; Kolesnikova, S. a.; Dmitrenok, P. S.; Bode, A.; Dong, Z.; Stonik, V. a. *Tetrahedron Letters* 2005, 46, 559-562). However, in recent publications where this synthetic strategy has been used to couple hydroquinone to geraniol, reaction yields ranges from 28 to 34% (Takenaka, K.; Tanigaki, Y.;

Patil, M. L.; Rao, C. V. L.; Takizawa, S.; Suzuki, T.; Sasai, H. *Tetrahedron: Asymmetry* 2010, 21, 767-770; Baeza, E.; Catalán, K.; Peña-Cortés, H.; Espinoza, L. *Quím. Nova* 2012, 35, 523-526), on the other hand when coupling 2,4,5-trimethoxyphenol with geraniol a mixture of mono-coupled compounds is obtained with yields ranging from 13 to 15% (Baeza, E.; Catalan, K.; Villena, J.; Carrasco, H.; Cuellar, M.; Espinoza, L. *Journal of the Chilean Chemical Society* 2012, 57, 1219-1223).

Therefore, there is still a need for a synthesis process for obtaining linear derivative compounds from geranylorcinol with a good yield.

SUMMARY OF THE INVENTION

The present invention discloses a synthesis process for obtaining linear derivative compounds from geranylorcinol, said linear derivatives compounds from geranylorcinol, the acetylated derivative compounds thereof, the method for encapsulating the compounds in a polymer matrix and the use of such encapsulated compounds as antifungal against *Botrytis Cinerea*.

DETAILED DESCRIPTION OF THE INVENTION

The present invention discloses a synthesis process for obtaining linear derivative compounds from geranylorcinol, said linear derivative compounds from geranylorcinol, the acetylated derivative compounds thereof, the method for encapsulating the compounds in a polymer matrix and the use of said encapsulated compounds as antifungal against *Botrytis cinerea*.

The synthesis process comprises condensation of geraniol with orcinol (Friedel-Crafts allylation) catalysed by a Lewis acid. The process comprises using the Lewis acid $BF_3 \cdot Et_2O$— catalyzed direct alkylation technique and the use of a $AgNO_3$ secondary catalyst employed for the first time in this type of reactions.

The synthesis process allowed the di-coupled derivative compounds represented by the formulas 1 to 4 to be obtained, from which the compounds of formula 2 and 4 correspond to compounds claimed in the present invention. The structures of the linear geranylorcinoles, obtained by the coupling method of the present invention, using the secondary $AgNO_3$ catalyst are shown in formulas 1 to 4.

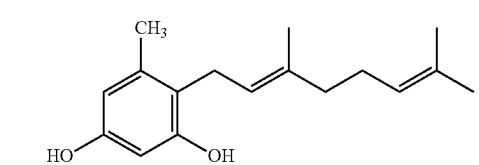

Formula 1

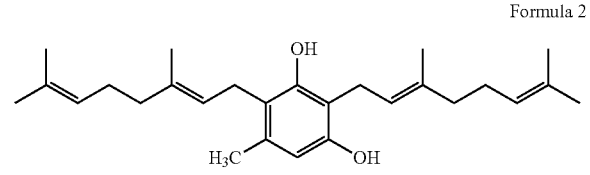 [SMILES: CC(C)=CCC/C(C)=C/Cc1c(C)cc(O)c(C/C=C(\C)CCC=C(C)C)c1O]

Formula 2

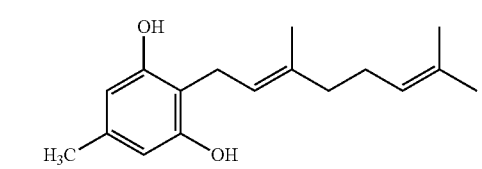

Formula 3

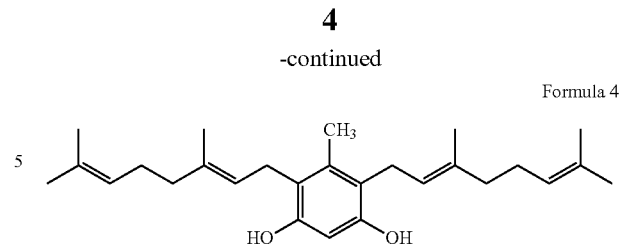

Formula 4

The compounds derived from the formulas 1 and 3, were previously synthesized by other authors (Manners, G.; Jurd, L.; and Stevens, K.; *Tetrahedron*, 1972, 28, 2949-2959; Eisohly, H. N.; Turner, C. E.; Clark, A. M.; and Eisohly, M. A.; *J. Pharmaceutical Sciences*, 1982, 71, 1319-1323) with yields of between 2-18% and also previously described by our research group, with yields of 12.6% and 27.6% for the derived compound 3 and 1 (Taborga, L., Vergara, A., Fernández, MJ, Osorio, M, Carvajal, M, Madrid, A, Marilaf, F, Carrasco, H, and Espinoza, *Journal of the Chilean Chemical Society*, 2013, 58, 1790-1796).

Additionally, the acetylated derivative compounds of the four compounds represented in formulas 1 to 4, which have been represented by formulas 5 to 8, respectively, were prepared. Formulas 5 to 8, correspond to the following structures:

Formula 5

Formula 6

Formula 7

Formula 8

The acetylated derivative compounds 5 to 8 correspond to structures claimed in the present invention. These derivative compounds were obtained from the respective geranylorcinol derivative compounds of formulas 1 to 4, through acetylation reaction under standard conditions; that is, by acetylation with acetic anhydride, 4-N,N-dimethylaminopyridine (DMAP) as catalyst and dichloromethane ($CH_2Cl_2$) as the solvent.

Experimental Procedure
Synthesis Process of the Geranylorcinol Derived Compounds of the Formulas 1, 2, 3 and 4

2 mL of acetonitrile was added to a solution of orcinol (1.22 g, 9.8 mmol) and geraniol (1.51 g, 9.8 g), and a solution of acetonitrile saturated in $AgNO_3$ (400 mg in 2 mL) was added thereafter, and then stirred at room temperature under a nitrogen atmosphere. $BF_3Et_2O$ (0.46 g, 3.2 mmol) was directly and slowly (dropwise) injected to this mixture. It was allowed to stir for 48 hours. The term of the reaction was monitored by thin layer chromatography (TLC). To complete the reaction, crushed ice (about 30 g) and abundant salt (about 50 g NaCl) were added, then vacuum filtered and the organic phase was extracted with AcOEt (3×20 mL), which phase was then washed with a solution of $NaHCO_3$ (15 mL, 5%) and water (2×15 mL), then dried over anhydrous $Na_2SO_4$, this solution was then filtered and evaporated to dryness. The reaction was performed in quadruplicate and the sum of crude reaction product was purified by column chromatography (CC) using silica gel (silica gel 60 for column chromatography, 0.040-0.063 mm) as the stationary phase and a mixture of acetate as the mobile phase (0:20→6:14:starting with a first addition with a total volume of 20 mL of hexane and 0 mL of ethyl acetate, the second addition of the same total volume, but now with 18.8 mL of hexane and 0.2 mL of ethyl acetate, and so on by increasing the amount of ethyl acetate in 0.2 mL and decreasing the amount of hexane in 0.2 mL in each fraction, until the last addition of 6 mL of hexane and 14 mL of ethyl acetate is reached, always maintaining a total and constant volume of 20 mL). A total of 108 fractions were collected in 10 mL flasks. Then, in order to identify the fractions containing the products, a qualitative analysis was performed by Thin Layer Chromatography (TLC) where fractions from 18-28 contained compound 2. They were combined and labelled as F-I 1,554.8 mg (9.9% yield) of a dark yellow viscous oil (formula 2 compound). Fractions from 38-49 were combined and contained compound 3, labelled F-II 1281.8 mg (12.5% yield) of a yellow viscous oil (formula 3 compound). Fractions from 67-73 were combined and contained the compound 4, labelled F-III 955.3 mg (6.1% yield) of a dark yellow viscous oil (formula 4 compound). Fractions from 74-76 were combined and contained the mixture of compounds 1 and 4, labelled F-IV 415.4 mg of a dark yellow viscous oil (mixture of compounds of formula 1 and 4, in a 0.125:1 ratio respectively). Fractions from 77-87 were combined and contained compound 1, labelled F-V 2816.2 mg (27.6% yield) of a yellow viscous oil (formula 1 compound). From fractions 88-108, the starting material (orcinol) which did not react (78.6 mg) was recovered.

Formula 1 Compound Spectroscopic Characterization:

RMN of $^1H$: 6.26 (s, 1H, H-6); 6.22 (s, 1H, H-2); 5.60 (bs. 2H, OH); 5.13 (t, J=6.8 Hz, 1H, H-2'); 5.05 (t, J=6.7 Hz, 1H, H-6'); 3.28 (d, J=6.7 Hz, 2H, H-1'); 2.21 (s, 3H, H-7); 2.09-2.06 (m, 2H, H-5'); 2.04-2.00 (m, 2H, H-4'); 1.78 (s, 3H, CH3-C3'); 1.67 (s, 3H, H-8'); 1.58 (s, 3H, CH3-C7'); RMN of $^{13}C$: 155.2 (C-3); 154.1 (C-1); 138.6 (C-5); 137.2 (C-3'); 131.8 (C-7'); 123.9 (C-6'); 122.2 (C-2'); 118.1 (C-4); 109.7 (C-6); 101.0 (C-2); 39.6 (C-4'); 26.4 (C-5'); 25.6 (C-8'); 25.0 (C-1'); 20.0 (C-7); 17.6 (CH3-C7'); 16.1 (CH3-C3'); IR (cm$^{-1}$): 3,393, 2,975, 2,925, 2,859, 1,602; EM (m/z, %): M$^+$ 260 (21.7), 137 (100), 191 (26.9), 177 (13.9), 123 (10.5).

Formula 2 Compound Spectroscopic Characterization:

RMN of $^1H$: 6.30 (s, 1H, H-6); 5.50 (s, 1H, OH); 5.44 (bs. 1H, OH); 5.32 (t, J=6.9 Hz, 1H, H-2'); 5.19 (t, J=6.6 Hz, 1H, H-2''); 5.11 (t, J=6.6 Hz, 2H, H-6' y H-6''); 3.46 (d, J=6.9 Hz, 2H, H-1'); 3.35 (d, J=6.6 Hz, 2H, H-1''); 2.25 (s, 3H, C$\underline{H}_3$—Ar); 2.16-2.15 (m, 4H, H-5' y H-5''); 2.12-2.09 (m, 4H, H-4' y H-4''); 1.86 (s, 3H, C$\underline{H}_3$—C3'); 1.84 (s, 3H, C$\underline{H}_3$—C3''); 1.73 (s, 6H, C$\underline{H}_3$—C7' y C$\underline{H}_3$—C7''); 1.64 (s, 6H, H-8' y H-8''); RMN of $^{13}C$: 153.4 (C-3); 152.5 (C-1); 138.3 (C-3'); 137.0 (C-3''); 135.1 (C-5); 131.8 ($^+$C-7'); 131.6 ($^+$C-7''); 123.9 ($^{++}$C-6'); 123.8 ($^{++}$C-6''); 122.5 (C-2''); 122.0 (C-2'); 118.1 (C-4); 111.5 (C-2); 109.7 (C-6); 39.6 (C-4'); 39.5 (C-4''); 26.4 ($^{+++}$C-5); 26.3 ($^{+++}$C-5'); 25.6 (C-8' y C-8''); 25.4 (C-1''); 22.5 (C-1'); 19.7 (C$\underline{H}_3$—Ar); 17.6 (C-10' y C-10''); 16.1 (C-9'); 16.0 (C-9''); IR (cm$^{-1}$): 3,454, 2,967, 2,917, 2,855, 1,747, 1,621, 1,592, 1,448, 1,377.

Formula 3 Compound Spectroscopic Characterization:

RMN of $^1H$: 6.26 (s, 2H, H-6 y H-4); 5.66 (bs. 2H, OH); 5.29 (t, J=6.6 Hz, 1H, H-2'); 5.08 (t, J=6.1 Hz, 1H, H-6'); 3.42 (d, J=7.0 Hz, 2H, H-1'); 2.20 (s, 3H, C$\underline{H}_3$—Ar); 2.13-2.10 (m, 2H, H-5'); 2.09-2.07 (m, 2H, H-4'); 1.83 (s, 3H, C$\underline{H}_3$—C3'); 1.70 (s, 3H, H-8'); 1.61 (s, 3H, C$\underline{H}_3$—C7'); RMN of $^{13}C$: 154.8 (C-1 y C-3); 138.6 (C-3'); 137.3 (C-5); 131.9 (C-7'); 123.7 (C-6'); 121.8 (C-2'); 110.6 (C-2); 109.0 (C-4 y C-6); 39.6 (C-4'); 26.3 (C-5'); 25.6 (C-8'); 22.1 (C-1'); 21.0 (C$\underline{H}_3$—Ar); 17.6 (C$\underline{H}_3$—C7'); 16.0 (C$\underline{H}_3$—C3'); IR (cm$^{-1}$): 3,455, 2,966, 2,922, 2,852, 1,772.

Formula 4 Compound Spectroscopic Characterization:

RMN of 1H: 6.25 (s, 1H, H-2); 5.12 (t, J=6.4 Hz, 2H, H-2'); 5.05 (t, J=6.6 Hz, 2H, H-6'); 3.33 (d, J=6.6 Hz, 4H, H-1'); 2.21 (s, 3H, C$\underline{H}_3$—Ar); 2.09-2.06 (m, 4H, H-5'); 2.03-2.00 (m, 4H, H-4'); 1.78 (s, 6H, C$\underline{H}_3$—C3'); 1.66 (s. 6H, H-8'); 1.58 (s, 6H, C$\underline{H}_3$—C7'); RMN of $^{13}C$: 152.9 (C-1 y C-3); 136.7 (C-3'); 136.4 (C-5); 131.7 (C-7'); 124.0 (C-6'); 122.6 (C-2'); 118.5 (C-4 yC-6); 101.4 (C-2); 29.6 (C-4'); 26.5 (C-5'); 25.7 (C-8'); 25.6 (C-1'); 17.6 (C$\underline{H}_3$—C7); 16.2 (C$\underline{H}_3$—C3'); 15.8 (C$\underline{H}_3$—Ar); IR (cm$^{-1}$): 3,404, 2,967, 2,922, 2,855, 1,649, 1,599, 1,445, 1,376.

Synthesis Process of the Geranylorcinol Acetylated Derived Compounds of the Formulas 5, 6, 7 and 8.

From each compound one portion (362 mg of the compound of formula 1; 170 mg of the formula 2 compound; 74 mg of the formula 3 compound; and 245 mg of the formula 4 compound) were taken which were separately placed in four reaction balloons with 50 mL of $CH_2Cl_2$, and then 1.0 mL of acetic anhydride and 2 crystals of 4-N,N-dimethylaminopyridine (DMAP) were added to each balloon. Then each mixture was allowed to stir for about one hour. After completion of the reaction the solution in each balloon was evaporated to dryness and re-suspended in 50 mL of ethyl acetate, which was washed with 30 mL of a 5% sodium bicarbonate solution and water (2×20 mL), then dried over anhydrous sodium sulphate (20 g), filtered and evaporated to dryness. Finally, the four compounds represented by formulas 5 to 8 were obtained with the following yields: Compound 5: 444.6 mg (92.8% yield) of a dark yellow viscous oil. Compound 6: 185 mg (90.5% yield) of a dark yellow viscous oil. Compound 7: 93.3 mg (96.4% yield) of a dark yellow viscous oil. Compound 8: 267.5 mg (89.8% yield) of a dark yellow viscous oil.

Formula 5 Compound Spectroscopic Characterization:

RMN of $^1H$: 6.80 (s, 1H, H-6); 6.70 (s, 1H, H-2); 5.04 (t, J=6.3 Hz, 1H, H-6'); 4.97 (t, J=6.4 Hz, 1H, H-2'); 3.21 (d, J=6.4 Hz, 2H, H-1'); 2.28 (s, 6H, COCH$_3$×2); 2.26 (s, 3H, CH$_3$—Ar); 2.06-2.02 (m, 2H, H-5'); 1.99-1.95 (m, 2H, H-4'); 1.73 (s, 3H, CH$_3$—C3'); 1.65 (s, 3H, H-8'); 1.58 (s, 3H, CH$_3$—C7'); RMN of $^{13}C$: 169.3 (COCH$_3$); 169.2 (COCH$_3$); 149.0 (C-3); 148.3 (C-1); 139.2 (C-5); 135.7 (C-3'); 131.4 (C-7'); 129.7 (C-4); 124.1 (C-6'); 121.2 (C-2'); 120.8 (C-6); 113.5 (C-2); 39.4 (C-4'); 26.5 (C-5'); 25.8 (C-8'); 25.6 (C-1'); 21.1 (COCH$_3$); 20.9 (COCH$_3$); 19.7

($CH_3$—Ar); 17.6 ($CH_3$—C7'); 16.2 ($CH_3$—C3'). IR ($cm^{-1}$): 2,968, 2,927, 2,851, 1,774, 1,752, 1,367; EM (m/z, %): 274 (10.8), 259 (4.1), 192 (12.3), 191(100), 176 (8.3).

Formula 6 Compound Spectroscopic Characterization:

RMN of $^1H$: 6.79 (s, 1H, H-6); 5.08-5.04 (m, 3H, H-6', H-6" y H-2'); 5.00 (t, J=7.0 Hz, 1H, H-2"); 3.17 (bs. 4H, H-1' y H-1"); 2.28 (s, 3H, $COCH_3$); 2.26 (s, 6H, $COCH_3$ y $CH_3$—Ar); 2.08-2.04 (m, 4H, H-5' y H-5"); 2.00-1.96 (m, 4H, H-4' y H-4"); 1.73 (s, 3H, *$CH_3$—C3'); 1.71 (s, 3H, *$CH_3$—C3"); 1.67 (s, 6H, H-8' y H-8"); 1.59 (s, 6H, $CH_3$—C7' y $CH_3$—C7"); RMN of $^{13}C$: 169.3 ($COCH_3$); 169.0 ($COCH_3$); 148.1 (C-3); 147.2 (C-1); 136.2 (C-5); 135.4 ($^+$C-3'); 135.2 ($^+$C-3"); 131.3 (C-7' y C-7"); 130.2 (C-4); 124.1 (C-6' y C-6"); 123.9 (C-2); 121.8 (C-6); 121.5 ($^{++}$C-2'); 121.4 ($^{++}$C-2"); 39.5 (C-4' y C-4"); 26.5 (C-5' y C-5"); 26.4 (C-1"); 25.6 (C-8' y C-8"); 24.2 (C-1'); 20.8 ($COCH_3$); 20.5 ($COCH_3$); 19.4 ($CH_3$—Ar); 17.6 ($CH_3$—C7' y $CH_3$—C7"); 16.1 ($^{+++}CH_3$—C3"); 16.0 ($^{+++}CH_3$—C3').

Formula 7 Compound Spectroscopic Characterization:

RMN of $^1H$: 6.77 (s, 2H, H-4 y H-6); 5.06 (t, J=6.3 Hz, 1H, H-6'); 5.02 (t, J=6.9 Hz, 1H, H-2'); 3.14 (d, J=6.9 Hz, 2H, H-1'); 2.32 (s, 3H, $CH_3$—Ar); 2.27 (s, 6H, $COCH_3$); 2.07-2.01 (m, 2H, H-5'); 1.97-1.93 (m, 2H, H-4'); 1.71 (s, 3H, $CH_3$—C3'); 1.66 (s, 3H, H-8'); 1.58 (s, 3H, $CH_3$—C7'); RMN of $^{13}C$: 169.1 ($COCH_3$×2); 149.4 (C-1 y C-3); 137.0 (C-5); 135.5 (C3'); 131.2 (C-7'); 124.0 (C-6'); 123.3 (C-2); 121.2 (C-2'); 120.8 (C-4-C-6); 39.5 (C-4'); 26.5 (C-5'); 25.6 (C-8'); 23.6 (C-1'); 20.9 ($CH_3$—Ar); 20.8 ($COCH_3$×2); 17.6 ($CH_3$—C7'); 16.1 ($CH_3$—C3').

Formula 8 Compound Spectroscopic Characterization:

RMN of $^1H$: 6.70 (s, 1H, H-2); 5.06 (t, J=6.2 Hz, 2H, H-6'); 5.01 (t, J=5.6 Hz, 2H, H-2'); 3.26 (d, J=6.2 Hz, 4H, H-1'); 2.28 (s, 6H, $COCH_3$); 2.22 (s, 3H, $CH_3$—Ar); 2.08-2.05 (m, 4H, H-5'); 2.01-1.98 (m, 4H, H-4'); 1.75 (s, 6H, $CH_3$—C3'); 1.67 (s, 6H, H-8'); 1.60 (s, 6H, $CH_3$—C7'); RMN of $^{13}C$: 169.2 ($COCH_3$×2); 146.8 (C-1 y C-3); 137.9 (C-5); 135.3 (C-3'); 131.2 (C-7'); 130.0 (C-4 y C-6); 124.0 (C-6'); 121.6 (C-2'); 113.9 (C-2); 39.4 (C-4'); 26.4 (C-5'); 26.2 (C-1'); 25.5 (C-8'); 20.7 ($COCH_3$×2); 17.5 ($CH_3$—C7'); 16.0 ($CH_3$—C3'); 15.4 ($CH_3$—Ar).

Evaluation of the Antifungal Activity of the Compounds Synthesized Against Botrytis Cinerea in Free State and Encapsulated System.

Preparation of the Stock Solution of Each Synthesized Compound without Encapsulating.

20-40 milligrams of each of compounds 1 to 8 were dissolved in 500 microliters of Ethanol to have a stock solution of each compound according to its molecular weight. The stock solution was diluted in 5 mL of water so as to obtain a new stock solution of 5,000 ppm; from which corresponding aliquots were taken to achieve a final concentration on each plate with 50, 150 and 250 ppm potato dextrose agar (PDA) culture medium.

Preparation of Stock Solution of Each Compound Synthesized in a Polymer Solution Pluronic F-127.

The method used for the preparation of polymeric micelles, based on Polycaprolactone (MW: 3.409 g/mol) or Pluronic® F-127 (MW: 12,500 g/mol) corresponds to the direct dissolution method consisting of the addition of the polymer to water with stirring and at room temperature, until the polymer dissolves to give a clear aqueous solution. The amount of polymer and water is chosen so as to have a solution of a concentration of $1\times10^{-3}$ M of polymer chains.

For the preparation of a solution of 50 mL of Pluronic F-127, 0.63 g is used and for the case of polycaprolactone 0.17 g is used.

The physical encapsulation of the compounds in the polymeric micelles ($1\times10^{-3}$ M) is carried out by the emulsion method. The compound is dissolved in a volatile solvent (dichloromethane) and 10 mL of the polymer solution added in 100 µL aliquots to complete 400 µL reaching a concentration of 0.101 M of compound. By stirring in a vortex and applying ultrasound a very homogeneous milky emulsion is formed. The organic solvent is then removed by evaporation by heating the emulsion at 50° C. in a system open to air. Upon removal of the solvent, a clear solution remains containing the polymer forming micelles and the non-polar compounds which have been encapsulated in the hydrophobic micro-domain provided by the core of these polymeric micelles.

Subsequently, the solution is diluted by adding polymer solution corresponding to a $1\times10^{-3}$ M concentration until the compound of interest reaches a stock concentration in the range of 625-1,250 ppm in the micelle to be applied to the plate. This dilution should be done by adding polymer solution so as to maintain the same concentration of micelles and vary only the concentration of active ingredient.

Anti-Phytopathogenic Activity Test Against B. cinerea.

In order to determine the inhibition of mycelial growth of B. cinerea, both for the free state and encapsulated compounds, the radial growth method in potato dextrose agar (PDA) culture medium was used. The compounds of interest in both free and encapsulated form were added to the PDA at different concentrations of 50, 150 and 250 ppm at a temperature of 50° C. Once the PDA had been solidified, a 4-mm diameter disc was seeded with mycelium of the pathogen in the center of the petri dish. The experiment consists of a negative control which is a petri dish where PDA culture medium and 1% Ethanol were added, in the case of Negative Control for encapsulated compounds it consists in adding only the micelle (polycaprolactone or Pluronic F-167) free in PDA. In addition, a positive control containing commercially available fungicide Captan in PDA culture medium is included at the same concentrations tested in both its free form and also a positive control of Captan in its encapsulated form. Each treatment consisted of three replicates (n=3 replicates/compound/concentration).

After 48 (free state) and 72 (encapsulated system) hours of incubation at 23° C. under a photoperiod of 16 light hours/8 darkness hours, the mycelial growth inhibition percentage (MGIP) was calculated by assessing the measurement of the diameter of the fungus growth around the disc to calculate the mycelial growth inhibition area. In this way, the mycelial growth inhibition percentage that was compared to the corresponding controls after 48 hours of incubation was determined.

Results

Table 1 shows that all the compounds derived from formulas 1 to 8 in their free state affect the mycelial growth of the pathogenic fungus B. cinerea in vitro between 51-97% at concentrations ranging from 150 to 250 ppm, as compared to the negative control after 48 hours of incubation. Compound 6 was found to be the most active by inhibiting mycelial growth by 97% at 250 ppm. The inhibition result is directly dependent on the concentration in which it is applied against the pathogen.

The inhibitory capacity is increased when the compounds are encapsulated in polymeric micelles of different origin. In the case of compounds derived from formulas 2, 4, 6 and 8 the biological activity in vitro increases when encapsulated in micelles formed by Pluronic F-127 to obtain a percentage of mycelial inhibition at 50 ppm between 81-99% as compared to the negative control after 72 hours. However, when these compounds are encapsulated in polycaprolactone micelles, only the compound of formula 4 improves its biological activity by 93% at 50 ppm, whereas the compounds derived from formulas 2, 6 to 8 do not produce any inhibiting effect on the mycelium of the pathogen as they are encapsulated in caprolactone micelles.

In the case of the mono-coupled compound of formula 1 (previously described in the literature) its activity at lower concentrations is also slightly improved when encapsulated in polycaprolactone as compared to the control, unlike the mono-coupled compound of formula 3 (previously described in the literature) which was inactive against the mycelium of the fungus when encapsulated in polycaprolactone.

The results indicate that the biological activity of mycelial inhibition is improved when the compounds are encapsulated in polymeric micelles; depending on its structure, it may be inferred that for the di-coupled compounds derived from formulas 2, 4, 6 and 8 it is more effective to use a polymeric Pluronic F-127 micelle, since its activity becomes equal to the activity of the positive control.

In the case of mono-coupled compounds derived from formulas 1, 3, 5 and 7 their effectiveness will depend on their structural composition when encapsulated in a micelle of polycaprolactone diblock.

TABLE 1

Mycelial inhibition percentage of the compounds of formula 1-8 both in free system and in encapsulated form in Polycaprolactone and Pluronic F-127 at different concentrations in vitro.

| | Mycelial inhibition percentage of *Botrytis cinerea* in vitro (%) | | | | | | | | |
|---|---|---|---|---|---|---|---|---|---|
| | Free compound | | | Compounds encapsulated in Polycaprolactone (Diblock) | | | Compounds encapsulated in Pluronic F-127 (Triblock) | | |
| Compound | 50 ppm | 150 ppm | 250 ppm | 50 ppm | 150 ppm | 250 ppm | 50 ppm | 150 ppm | 250 ppm |
| Formula 1 | 0 | 25 | 75 | 37 | 61 | 73 | — | — | — |
| Formula 2 | 25 | 61 | 93 | 16 | 36 | 37 | 85 | 91 | 96 |
| Formula 3 | 37 | 65 | 82 | 9 | 32 | 42 | — | — | — |
| Formula 4 | 12 | 56 | 83 | 93 | 94 | 97 | 82 | 92 | 96 |
| Formula 5 | 24 | 55 | 78 | 16 | 39 | 80 | — | — | — |
| Formula 6 | 5 | 69 | 97 | 10 | 31 | 50 | 93 | 99 | 99 |
| Formula 7 | 8 | 51 | 82 | 32 | 35 | 59 | — | — | — |
| Formula 8 | 11 | 54 | 85 | 0 | 36 | 36 | 93 | 99 | 99 |
| C− (negative control) | 0 | 0 | 0 | 0 | 0 | 0 | 0 | 0 | 0 |
| C+ (positive control) | 87 | 94 | 94 | 93 | 99 | 99 | 98 | 99 | 99 |

(—): Not tested.

The invention claimed is:

1. An encapsulated compound, wherein said encapsulated compound is a polymeric micelle containing a compound selected from the group consisting of a compound of Formula 1, a compound of Formula 2, a compound of Formula 3, a compound of Formula 4, a compound of Formula 5, or a compound of Formula 6:

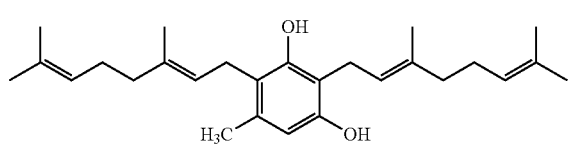

Formula 1

Formula 2

Formula 3

Formula 4

-continued

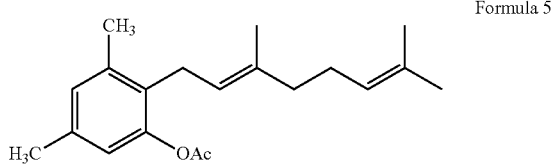

Formula 5

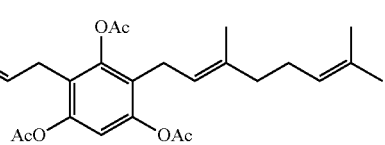

Formula 6

2. A method of preparing the encapsulated compound of claim 1, the method comprising:
   (i) dissolving the compound in a solvent;
   (ii) adding an aqueous polymer solution;
   (iii) stirring in a vortex and applying ultrasound until a homogeneous emulsion is formed; and
   (iv) removing the solvent by evaporation.

3. A method of treating a fungal infection in a subject, the method comprising:
   administering the encapsulated compound according to claim 1 as an antifungal agent, to the subject in need thereof having the fungal infection in an amount effective for treating the fungal infection.

4. The method according to claim 3, wherein said fungal infection is caused by *Botrytis cinerea*.

5. The encapsulated compound of claim 1, wherein the polymeric micelle consists of a polymer selected from polycaprolactone or Pluronic F-127.

6. The encapsulated compound of claim 1, wherein the compound is selected from the group consisting of a compound of Formula 1, a compound of Formula 2, a compound of Formula 4, or a compound of Formula 6.

7. The encapsulated compound of claim 1, wherein the encapsulated compound is formed by emulsion encapsulation.

* * * * *